United States Patent [19]

Chen

[11] Patent Number: 4,804,538
[45] Date of Patent: Feb. 14, 1989

[54] METHOD FOR PRODUCING POWDER CAKE COSMETICS

[75] Inventor: Mei L. Chen, Taipei, Taiwan

[73] Assignee: Misasa Inc., New York, N.Y.

[21] Appl. No.: 33,714

[22] Filed: Apr. 3, 1987

[51] Int. Cl.$^4$ .......................... A61K 6/00; B29C 39/12
[52] U.S. Cl. ...................................... 424/401; 424/63; 264/245
[58] Field of Search .......................... 424/401; 264/245

[56] References Cited

U.S. PATENT DOCUMENTS 1,707,684  4/1929  Picker ................................. 424/401
4,188,316  2/1980  Sawada ........................... 264/245 X

FOREIGN PATENT DOCUMENTS 0198411  11/1983  Japan .................................. 424/401
0212423  12/1984  Japan .................................. 424/401

Primary Examiner—Michael Lusignan
Attorney, Agent, or Firm—Klein & Vibber, P.C.

[57] ABSTRACT

A method for producing powder cosmetics which utilizes some suitable solvents to convert the powder materials into slurry form, so as to facilitate transportation through pipelines. The slurry is filled into a plastic case through an opening provided at its lower face and the solvent is discharged from the slurry at a reduced pressure. Thus, convert the slurry to a powder cake.

5 Claims, 3 Drawing Sheets

METHOD FOR PRODUCING POWDER CAKE COSMETICS

BACKGROUND OF THE INVENTION

The present invention relates to method for producing powder cake cosmetics and, more particularly, to a method for producing powder cake cosmetics which is carried out by first mixing powder materials with some solvents so as to change from a solid state to a slurry state for more convenient transportation through a pipeline. The slurry is set into powder cake after the separation of solvents.

Solids, in general, are more difficult to handle than liquids or gases. Heretofore, powder cake cosmetics such as eyeshadow, blush on, foundation, etc., have been provided in various colors. In most powder cake cosmetics industries, powder cake cosmetics are packed by using a powder press to press the color powders into metal pans. Several pans of pressed powders in different colors are selected and then manually installed into a cosmetic compact or casing.

The afore-described known method of packing possesses the following drawbacks:

1. a powder press is used, thus the process requires a larger amount of energy;
2. a metal pan is used, thus raising the production cost;
3. manual operation is required to select and install metal pans that have been filled with powder of different color into a cosmetic compact; and
4. only one color is completed during an operation.

Since these drawbacks arise from difficulties in solid handling, therefore, a change from solid state to slurry state is worth taking into consideration.

SUMMARY OF THE INVENTION

It is a primary object of the present invention to provide a convenient process for producing powder cake cosmetics.

Another object of the present invention is to provide a convenient method for filling powder cake cosmetics into a cosmetic compact.

A further object of the present invention is to provide a method for filling multi-color powder cake cosmetics in one step.

Another object of the present invention is to provide powder cake cosmetics which can be filled into a plastic case of any desired configuration with color selected.

Still another object of the present invention is to provide powder cake cosmetics which are cheaper with respect to the method of production.

BRIEF DESCRIPTION OF THE DRAWING

With these and other objects in view, which will become apparent in the following detailed description, the present invention, which is shown by example only, will be clearly understood in connection with the accompanying drawing, in which.

DETAILED DESCRIPTION OF THE PREFERRED EMBODIMENTS

Figure 1:
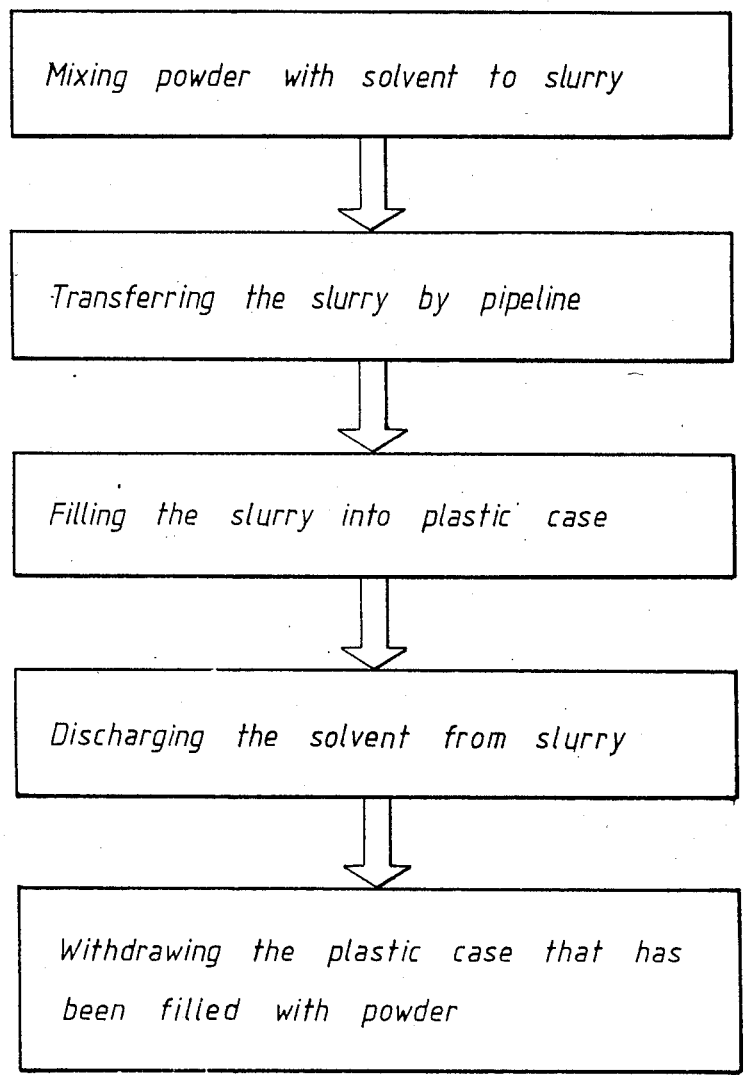
FIG. 1 is a block diagram illustrating a process in accordance with the present invention.

Referring first to FIG. 1, it can be seen that the present invention comprises a manufacturing procedure of mixing powder materials with some suitable solvents to form a slurry stock. The slurry can readily be transferred through pipelines. A constant output means is employed to conduct various slurries of different colors in a constant amount to a predetermined position so as to be ready for direct filling. Plastic cases in special designation to be filled with these slurries, are automatically positioned such that each slurry corresponds to each part of said case. Further, when slurries are filled into the bottom of said case, a discharge process is simultaneously carried out to separate the solvent and to convert the slurry back to a powder cake. Accordingly, the cases already filled with powder are withdrawn.

It should be noted that numerous different colored powders can be filled at one time by increasing the number of pipelines and constant output means to the same number as that of the different colored powders.

The improved process according to the present invention for producing powder cosmetics comprises the following steps:

Step 1
mixing at least 13 to 51% weight of powder material, coloring material and binder, with at least 87 to 49% weight of solvent, to form slurries in different colors;

Step 2
transferring the slurries by isobaric pipeline transportation at a safe pressure and room temperature to a predetermined position;

Step 3
filling the slurries into plastic cases;

Step 4
discharging the solvent from said slurries at a reduced pressure; and

Step 5
withdrawing the plastic cases that have been filled with powders.

Figure 2:
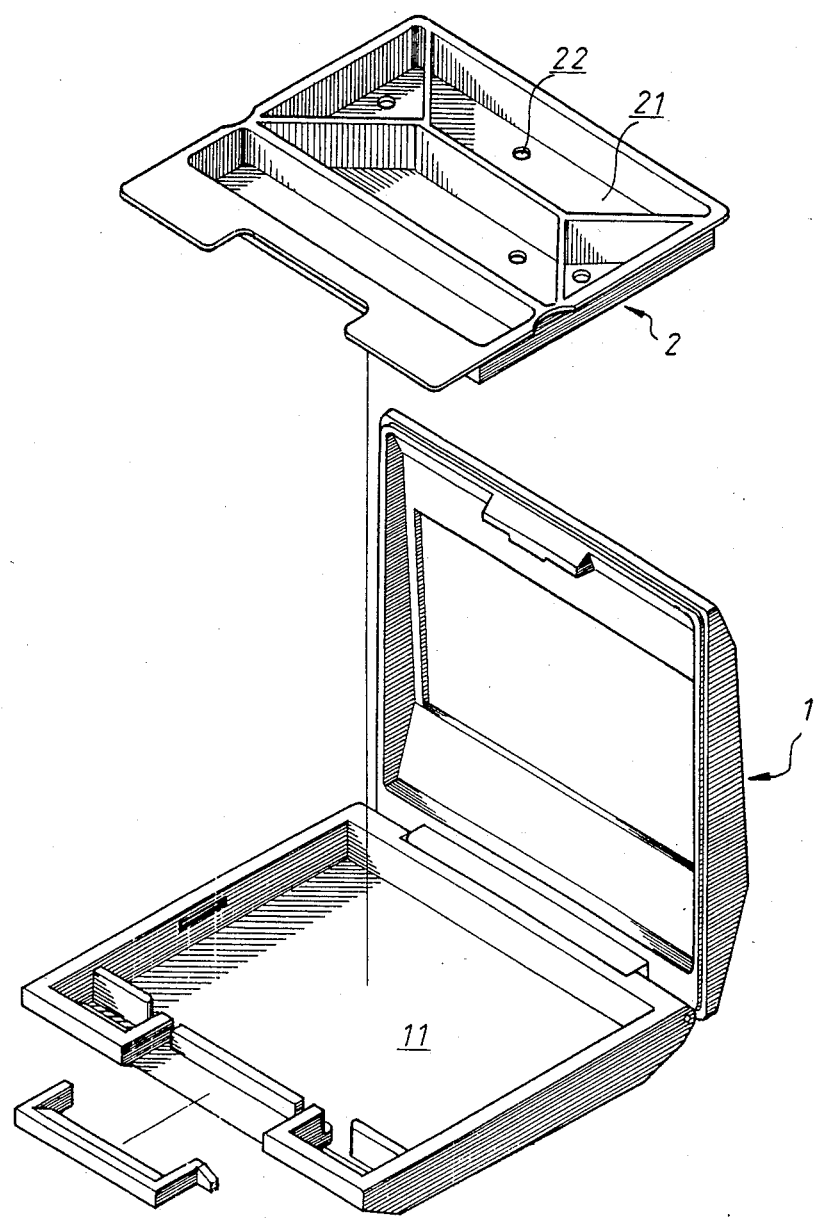
FIG. 2 illustrates a plastic case and a cosmetic compact used in accordance with the present invention.

Referring next to FIG. 2, an exemplary cosmetic compact 1 and plastic case 2 are shown perspectively. Said plastic case 2 is divided into a plurality of cavities 21 of the same or differing configurations. Each cavity 21 is provided with an opening 22 at the lower face thereof. After the plastic case 2 is filled with powders of various different colors, the whole plastic case 2 is installed into the recess 11 of the cosmetic compact 1.

Figure 3:
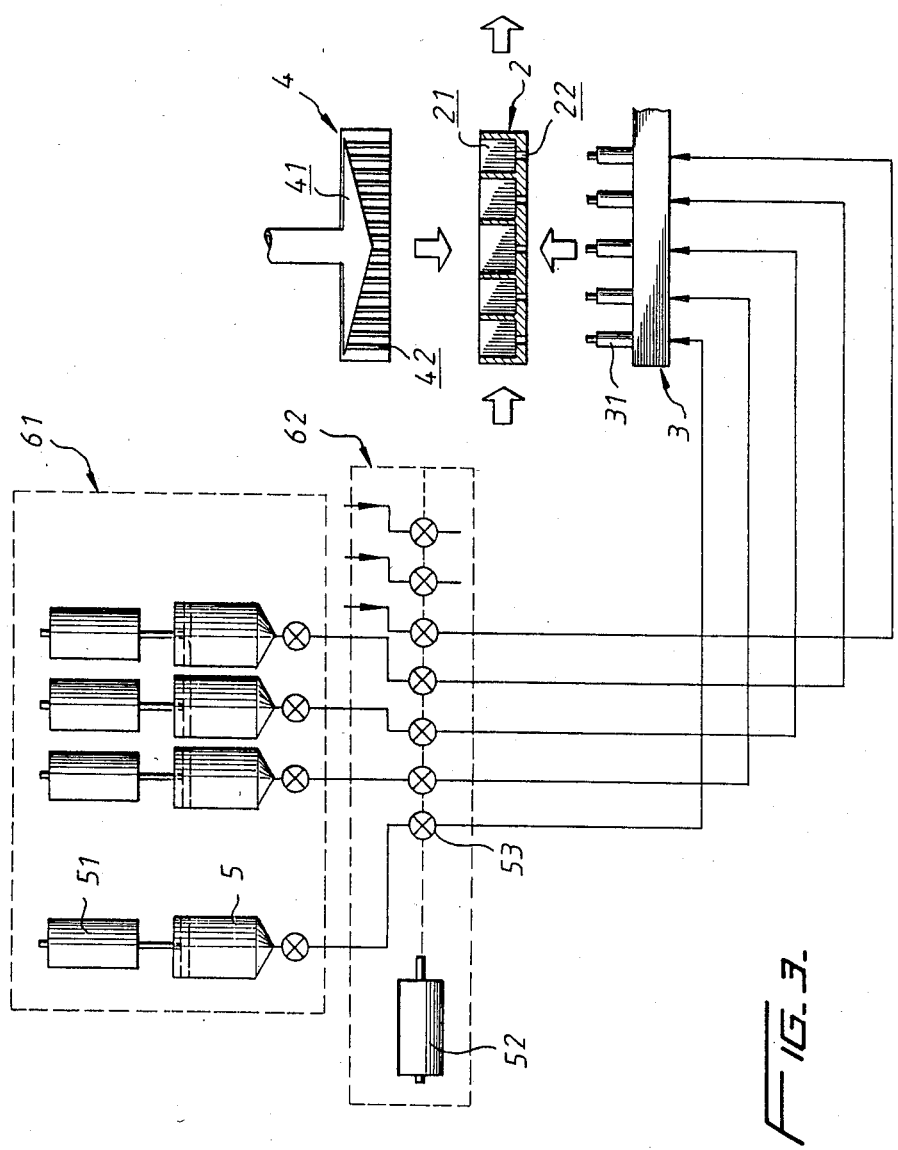
FIG. 3 is a flow diagram illustrating the process in accordance with the present invention.

Referring next to FIG. 3, it can be seen that the slurry transportation process is set up by a propulsive unit 61. Said propulsive unit 61 consists of a plurality of slurry hoppers 5 and their corresponding cylinders 51. Mixtures of powders and solvents are stored in said slurry hopper 5, wherefrom the slurry is conducted through pipelines connected at the bottom by exerting pressure into the interior of said slurry hoppers 5 by the cylinders 51 thereabove. A constant output process is then carried out and is set up by a constant output valve 62. Said constant output valve 62 consists of a cylinder 52 and a plurality of globe valves 53 corresponding to said slurry hoppers 5. Said cylinder 52 may open or close all globe valves 53 simultaneously by the interaction between the shaft of said cylinder 52 and the globe valves 53. In addition, a timer may be used to control the period of motion of said cylinder 52 in order to provide a constant output of slurry and fulfill the desired condition for filling the plastic case 2.

After passing through said constant output valve 62, the pipeline is connected to a filling station 3. The slurry is then conducted to filling nozzles 31 provided on said filling station 3. Accordingly, the filling station 3 is lifted upward such that each filling nozzle 31 is inserted into the corresponding opening 22 at the base of the plastic case 2 so as to fill the plastic cases 2 with slurries.

A discharge mechanism 4 is employed to separate the solvent from said slurries. In a preferred embodiment, the discharge mechanism has a discharge cavity 41 in the interior thereof. The discharge cavity 41 has several discharge flues 42 which extend to the bottom face of said discharge mechanism 4. In this process, a cylinder impelling mechanism may also be employed to compress the top face of the plastic case 2 in order to separate solvent remaining in cavities 21 of the plastic case 2 and set into a powder cake finally. When this process is completed, plastic case 2 is withdrawn from the system.

The present invention has the following advantages:

1. Use of metal pans can be eliminated because the powder is filled directly into the cavity through the opening of the plastic case and capital investment can thus be lowered;
2. A single filling machine can provide multi-color filling;
3. The plastic case can be constructed in any desirable configuration; and
4. Manual operation is no longer necessary, since the whole operation is carried out automatically, thereby achieving a higher efficiency and a safe and hygienic production.

Useful "powder materials" include talc, titanium dioxide, Kaolin, mica, magnesium stearate, and the like and may include some pearlescence substance which can be a mixture of titanium dioxide and mica, titanium dioxide and mica and iron oxide, titanium dioxide and mica and carmine, and the like.

Useful "coloring materials" can be inorganic pigments such as iron oxide, ultramarine blue, chromium pigment, etc., and/or organic pigments such as D&C Red No. 6 Barium Lake, D&C Red No. 7 Calcium Lake, FD&C Red No. 3 Aluminum Lake, D&C Red No. 21, D&C Red No. 27 Aluminum Lake, etc.

Useful "binders" include dimethicon, lanolin, mineral oil, squalane and hydrophilic polymeric oil. Particles of various powder materials are held in adhesion by these binders.

"Solvents" useful in this invention can be alcoholic solvents, low boiling point hydrocarbon or low boiling point cyclic silicon oil. This component is especially important in this invention in that it mixes with other materials to form a slurry stock.

Other additives such as preservatives, antioxidant, perfume, surfactant, etc., can also be added if necessary.

Two examples are provided hereinafter and are directed to better illustrate the invention in a non-limitative way.

| Composition | Weight percent |
|---|---|
| Example 1   EYE SHADOW | |
| 1. Talc | 10.2 |
| 2. Titanium Dioxide | 5.0 |
| 3. Kaolin | 3.5 |
| 4. Mica | 13.0 |
| 5. Aluminum Hydroxide | 10.0 |
| 6. Mineral oil | 4.0 |
| 7. Lanolin | 2.0 |
| 8. Isopropyl Isostearate | 6.0 |
| 9. Dimethicon | 2.0 |
| 10. Propylparaben | 0.1 |
| 11. Yellow Iron Oxide | 1.2 |
| 12. Red Iron Oxide | 2.5 |
| 13. Ultramarine Violet | 3.4 |
| 14. Manganese Violet | 2.1 |
| 15. Titanium Dioxide & Mica | 15.0 |
| 16. Titanium Dioxide & Mica & Carmine | 20.0 |
| Example 2   BLUSH ON | |
| 1. Talc | 35.395 |
| 2. Titanium Dioxide | 8.0 |
| 3. Kaolin | 2.0 |
| 4. Mica | 30.0 |
| 5. Aluminum Hydroxide | 5.0 |
| 6. Mineral oil | 2.0 |
| 7. Lanolin | 0.5 |
| 8. Dimethicon | 2.0 |
| 9. Squalane | 4.0 |
| 10. Propylparaben | 0.1 |
| 11. B.H.A. | 0.005 |
| 12. Yellow Iron Oxide | 2.7 |
| 13. Red Iron Oxide | 1.8 |
| 14. D & C Red 7 Ca. lake | 0.5 |
| 15. Titanium Dioxide & Mica | 3.5 |
| 16. Titanium Dioxide & Mica & Iron Oxide | 2.5 |

Although the invention is described and illustrated with reference to a plurality of embodiments thereof, it is to be expressly understood that it is in no way limited to the disclosure of such preferred embodiments but is capable of numerous modifications within the scope of the appended claims.

I claim:

1. A method for producing powder cake cosmetics comprising the steps of:
   (a) mixing at least a mixture of powder materials, coloring materials and binders with at least a solvent, to form a slurry;
   (b) delivering said slurry through a pipeline to a predetermined position;
   (c) filling the slurry into a cavity of a plastic case, each cavity being provided with an opening at a lower face thereof which connects said pipeline at said predetermined position;
   (d) discharging the solvent from said slurry at a reduced pressure; and
   (e) withdrawing the plastic case that has been filled with powder cosmetics.

2. A method as claimed in claim 1, wherein said mixture of powder materials, coloring materials, and binders, further comprises a small amount of additives.

3. A method as claimed in claim 1, wherein said powder materials are selected from the group consisting of talc, titanium dioxide, Kaolin, mica, magnesium stearate, iron oxide, and carmine.

4. A method as claimed in claim 1, wherein said binders are selected from the group consisting of dimethicon, lanolin, mineral oil, squalane, and hydropholic polymeric oil.

5. A method as claimed in claim 1, wherein said solvents are selected from the group consisting of alcoholic solvents, low boiling point hydrocarbons, and low boiling point cyclic silicon oil.

* * * * *